US011141333B2

(12) United States Patent
Kloka

(10) Patent No.: US 11,141,333 B2
(45) Date of Patent: Oct. 12, 2021

(54) PATIENT TRANSPORT APPARATUS WITH HANDLE ASSEMBLY FOR CONTROLLING DRIVE SYSTEM

(71) Applicant: Stryker Corporation, Kalamazoo, MI (US)

(72) Inventor: Maksym Kloka, Buffalo, MN (US)

(73) Assignee: Stryker Corporation, Kalamazoo, MI (US)

( * ) Notice: Subject to any disclaimer, the term of this patent is extended or adjusted under 35 U.S.C. 154(b) by 337 days.

(21) Appl. No.: 16/210,848

(22) Filed: Dec. 5, 2018

(65) Prior Publication Data

US 2019/0183701 A1 Jun. 20, 2019

Related U.S. Application Data

(60) Provisional application No. 62/607,494, filed on Dec. 19, 2017.

(51) Int. Cl.
*A61G 7/018* (2006.01)
*A61G 7/08* (2006.01)
(Continued)

(52) U.S. Cl.
CPC ............. *A61G 7/018* (2013.01); *A61G 7/08* (2013.01); *A61G 7/1013* (2013.01);
(Continued)

(58) Field of Classification Search
CPC ........ A61G 7/018; A61G 7/08; A61G 7/1013; A61G 7/1019; A61G 7/1046
(Continued)

(56) References Cited

U.S. PATENT DOCUMENTS 6,772,850 B1 8/2004 Waters et al.
7,007,765 B2 * 3/2006 Waters ................. A61G 1/0237
180/19.3
(Continued)

FOREIGN PATENT DOCUMENTS

EP 1693035 A1 8/2006
WO 2005051277 A1 6/2005
(Continued)

OTHER PUBLICATIONS

English language abstract for WO 2005/051277 extracted from espacenet.com database on Feb. 12, 2019, 2 pages.

*Primary Examiner* — Robert G Santos
(74) *Attorney, Agent, or Firm* — Howard & Howard Attorneys PLLC

(57) ABSTRACT

A patient transport apparatus transports a patient over a surface. The patient transport apparatus comprises a support structure comprising a base, a patient support surface, and a reference sensor arranged to sense inclination of the support structure. A drive system is coupled to the support structure and operable to propel the patient transport apparatus. A handle assembly is operable by a user to control operation of the drive system. The handle assembly comprises a handle movable relative to the base and a position sensor arranged to sense positioning of the handle. A controller is coupled to the reference sensor and the position sensor, and is adapted to control the drive system in response to signals received from the reference sensor and the position sensor.

18 Claims, 7 Drawing Sheets

(51) Int. Cl.
*A61G 7/10* (2006.01)
*A61G 7/05* (2006.01)
*A61B 5/00* (2006.01)
*A61G 7/005* (2006.01)

(52) U.S. Cl.
CPC ..... *A61B 5/6892* (2013.01); *A61B 2562/0252* (2013.01); *A61G 7/005* (2013.01); *A61G 7/0528* (2016.11); *A61G 7/1046* (2013.01); *A61G 7/1067* (2013.01); *A61G 2203/14* (2013.01); *A61G 2203/32* (2013.01); *A61G 2203/42* (2013.01)

(58) Field of Classification Search
USPC ............... 5/613, 616, 600, 510, 86.1, 81.1 R
See application file for complete search history.

(56) References Cited

U.S. PATENT DOCUMENTS

| | | | |
|---|---|---|---|
| 7,419,019 B1 * | 9/2008 | White | A61G 7/08 180/19.1 |
| 7,789,187 B2 * | 9/2010 | Zerhusen | A61G 1/0237 180/323 |
| 7,827,634 B2 * | 11/2010 | Stroh | A61G 7/08 5/510 |
| 7,882,582 B2 * | 2/2011 | Kappeler | A61G 7/0528 5/600 |
| 7,886,377 B2 * | 2/2011 | Hamberg | A61G 1/0287 5/86.1 |
| 8,442,738 B2 * | 5/2013 | Patmore | A61G 7/0528 701/93 |
| 8,474,073 B2 * | 7/2013 | Hamberg | A61G 7/018 5/600 |
| 8,756,726 B2 * | 6/2014 | Hamberg | A61G 1/0268 5/86.1 |
| 9,259,369 B2 | 2/2016 | Derenne et al. | |
| 10,384,539 B2 * | 8/2019 | Steinhauser | A61G 7/05 |
| 10,406,044 B2 * | 9/2019 | Trepanier | A61G 1/0281 |
| 10,406,045 B2 * | 9/2019 | Hayes | A61G 1/0281 |
| 10,603,234 B2 * | 3/2020 | Puvogel | A61G 7/08 |
| 10,799,403 B2 * | 10/2020 | Paul | A61G 7/05 |
| 10,898,399 B2 * | 1/2021 | Paul | A61G 7/012 |
| 2004/0200646 A1 * | 10/2004 | Waters | B60L 3/0092 180/15 |
| 2007/0241529 A1 * | 10/2007 | Stroh | A61G 7/08 280/202 |
| 2007/0245488 A1 | 10/2007 | Zimbalista et al. | |
| 2008/0086815 A1 * | 4/2008 | Kappeler | A61G 7/0524 5/600 |
| 2008/0141459 A1 * | 6/2008 | Hamberg | A61G 1/0225 5/600 |
| 2009/0188731 A1 * | 7/2009 | Zerhusen | A61G 1/0281 180/19.3 |
| 2011/0087416 A1 * | 4/2011 | Patmore | B60L 50/20 701/93 |
| 2011/0126354 A1 * | 6/2011 | Hamberg | A61G 7/0528 5/600 |
| 2013/0318710 A1 * | 12/2013 | Hamberg | A61G 1/0287 5/425 |
| 2014/0076644 A1 | 3/2014 | Derenne et al. | |
| 2016/0367415 A1 * | 12/2016 | Hayes | A61G 1/02 |
| 2016/0374874 A1 * | 12/2016 | Trepanier | A61G 1/04 5/611 |
| 2017/0003159 A1 | 1/2017 | Kostic et al. | |
| 2017/0281440 A1 | 10/2017 | Puvogel et al. | |
| 2018/0194224 A1 * | 7/2018 | Steinhauser | A61G 7/08 |
| 2019/0183701 A1 * | 6/2019 | Kloka | A61G 7/1013 |
| 2019/0183703 A1 * | 6/2019 | Paul | A61G 7/018 |
| 2019/0201255 A1 * | 7/2019 | Paul | A61G 7/05 |
| 2019/0201256 A1 * | 7/2019 | Derenne | A61G 1/0287 |
| 2019/0298590 A1 * | 10/2019 | Patmore | A61G 1/0268 |
| 2020/0375829 A1 * | 12/2020 | Zerhusen | A61G 7/0506 |
| 2021/0100705 A1 * | 4/2021 | Paul | A61G 7/08 |

FOREIGN PATENT DOCUMENTS

| | | |
|---|---|---|
| WO | 2015021950 A1 | 2/2015 |
| WO | 2017001497 A1 | 1/2017 |

* cited by examiner

PATIENT TRANSPORT APPARATUS WITH HANDLE ASSEMBLY FOR CONTROLLING DRIVE SYSTEM

CROSS-REFERENCE TO RELATED APPLICATION

The subject patent application claims priority to and all the benefits of U.S. Provisional Patent Application No. 62/607,494 filed on Dec. 19, 2017, the disclosure of which is hereby incorporated by reference in its entirety.

BACKGROUND

Patient transport systems facilitate care of patients in a health care setting. Patient transport systems comprise patient transport apparatuses (e.g., a bed, stretcher, cot, recliner, wheelchair, etc.) to move patients between locations. A patient transport apparatus comprises a base, a patient support surface, and several support wheels, such as four swiveling caster wheels. A drive system is sometimes utilized to assist a caregiver in moving the patient transport apparatus over a floor surface.

Drive systems typically operate based on a caregiver pushing or pulling on one or more handles at a head end of the patient transport apparatus. Traditional drive systems utilize force sensors (load cells) coupled to the handle to determine the force with which the handle is being pushed or pulled. The amount of force applied to the handle determines the speed of the drive system. Load cells are expensive, and therefore this type of drive system may be underutilized in patient transport systems even where it may be desirable. However, in place of force sensors, other types of sensors may give inaccurate readings.

A patient transport apparatus designed to overcome one or more of the aforementioned challenges is desired.

DETAILED DESCRIPTION

Figure 1:
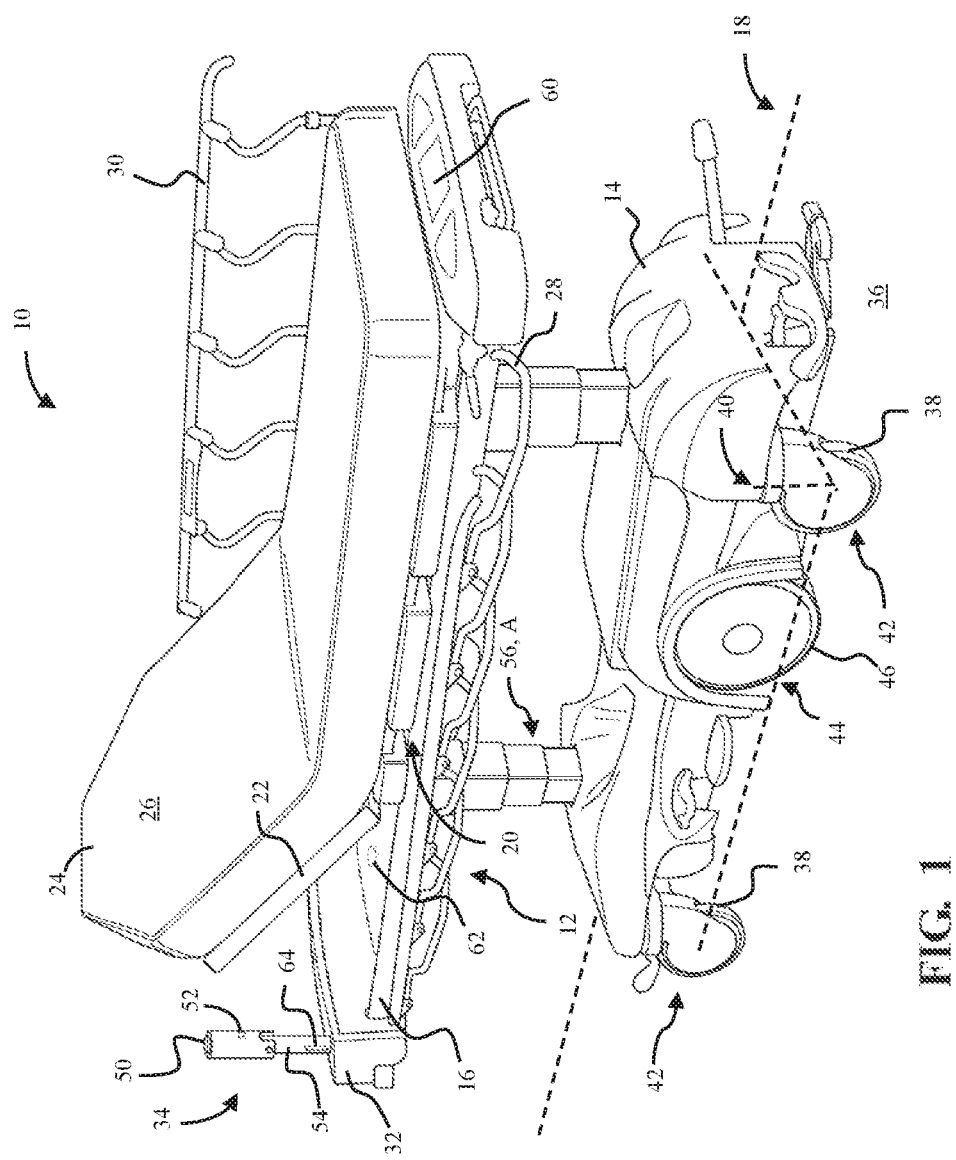
FIG. 1 is perspective view of a patient transport apparatus.

Referring to FIG. 1, a patient transport system comprising a patient transport apparatus 10 is shown for supporting a patient in a health care setting. The patient transport apparatus 10 illustrated in FIG. 1 comprises a stretcher. In other embodiments, however, the patient transport apparatus 10 may comprise a hospital bed, a cot, or similar apparatus (e.g., a recliner, wheelchair, etc.), utilized in the care of a patient to transport the patient between locations.

A support structure 12 provides support for the patient. The support structure 12 illustrated in FIG. 1 comprises a base 14 and an intermediate frame 16. The base 14 defines a longitudinal axis 18 from a head end to a foot end. The intermediate frame 16 is spaced above the base 14. The support structure 12 also comprises a patient support deck 20 disposed on the intermediate frame 16. The patient support deck 20 comprises several sections, some of which articulate (e.g., pivot) relative to the intermediate frame 16, such as a fowler section, a seat section, a thigh section, and a foot section. The patient support deck 20 provides a patient support surface 22 upon which the patient is supported.

A mattress 24 is disposed on the patient support deck 20. The mattress 24 comprises a secondary patient support surface 26 upon which the patient is supported. The base 14, the intermediate frame 16, the patient support deck 20, and the patient support surfaces 22, 26 each have a head end and a foot end corresponding to designated placement of the patient's head and feet on the patient transport apparatus 10. The construction of the support structure 12 may take on any known design, and is not limited to that specifically set forth above. In addition, the mattress 24 may be omitted in certain embodiments, such that the patient rests directly on the patient support surface 22.

Side rails 28, 30 are supported by the base 14. A first side rail 28 is positioned at a right side of the intermediate frame 16. A second side rail 30 is positioned at a left side of the intermediate frame 16. If the patient transport apparatus 10 is a stretcher, there may be fewer side rails. The side rails 28, 30 are movable between a raised position in which they block ingress and egress into and out of the patient transport apparatus 10 and a lowered position in which they are not an obstacle to such ingress and egress. The side rails 28, 30 may also be movable to one or more intermediate positions between the raised position and the lowered position. In still other configurations, the patient transport apparatus 10 may not comprise any side rails.

A headboard 32 is coupled to the intermediate frame 16. In other embodiments, when the headboard 32 is provided, the headboard 32 may be coupled to other locations on the patient transport apparatus 10, such as the base 14. In still other embodiments, the patient transport apparatus 10 does not comprise the headboard 32. A footboard (not shown) may also be coupled to the intermediate frame 16 or to other locations on the patient transport apparatus 10, such as the base 14.

A handle assembly 34 is shown integrated into the headboard 32 to facilitate movement of the patient transport apparatus 10 over floor surfaces 36. Additional caregiver interfaces, such as additional handles, may be integrated into other components of the patient transport apparatus 10, that may be graspable by the caregiver to manipulate the patient transport apparatus 10 for movement. A caregiver interface may additionally comprise a surface on the patient transport apparatus 10 upon which the caregiver logically applies force to cause movement of the patient transport apparatus 10 in one or more directions, also referred to as a push location. This could comprise one or more surfaces on or adjacent to the headboard 32, footboard (not shown), and/or the side rails 28, 30.

Support wheels 38 are coupled to the base 14 to support the base 14 on the floor surface 36, such as a hospital floor or other surface (e.g., any indoor or outdoor ground, road, sidewalk, etc.). The support wheels 38 allow the patient transport apparatus 10 to move in any direction along the floor surface 36 by swiveling to assume a trailing orientation relative to a desired direction of movement. In the embodiment shown, the support wheels 38 comprise four support wheels each arranged in corners of the base 14. The support wheels 38 shown are caster wheels able to rotate and swivel about swivel axes 40 during transport. Each of the support wheels 38 forms part of a caster assembly 42. Each caster assembly 42 is mounted to the base 14. It should be understood that various configurations of the caster assemblies 42 are contemplated. In addition, in some embodiments, the support wheels 38 are not caster wheels and may be non-steerable, steerable, non-powered, powered, or combinations thereof. Additional support wheels 38 are also contemplated.

A drive system 48 (FIG. 2) influences motion of the patient transport apparatus 10 during transportation over the floor surface 36. In one embodiment, the drive system comprises a drive wheel assembly 44 having one or more powered drive wheels 46 that are selectively driven. In some embodiments, the drive wheel assembly 44 may comprise other types of wheels or drive tracks. The drive system 48 has one or more motors M. The drive system 48 is integrated into the patient transport apparatus 10. For instance, the drive system 48 may be integrated into the base 14. The drive system 48 is operable to propel the patient transport apparatus 10 in one or more of a forward and rearward direction, and thereby reduces the amount of force required by a caregiver to push the patient transport apparatus 10 from one location to another. Further details of a drive system that may be used with the patient transport apparatus 10 disclosed herein are disclosed in commonly assigned U.S. Pat. No. 6,772,850, issued to Waters et al. and entitled POWER ASSISTED WHEELED CARRIAGES, as well as U.S. Pat. No. 9,259,369, issued to Derenne et al. and entitled POWERED PATIENT SUPPORT APPARATUS, the complete disclosures of which are both hereby incorporated herein by reference.

The handle assembly 34 is used to control the drive system 48. The handle assembly 34 may comprise one or more movable handles 50. The handles 50 may be movable, for instance, relative to the headboard 32, intermediate frame 16, and/or the base 14 (only one handle 50 is shown in FIG. 1). The handle assembly 34 also comprises a position sensor 52 arranged to sense positioning of the handle 50. The position sensor 52 may comprise an accelerometer. In one embodiment, the support structure 12 comprises a post 54 coupled to the handle 50 with the handle 50 being capable of pivoting relative to the post 54 via a pivot pin or the like. The post 54 is fixed to and extends upwardly from the intermediate frame 16. In alternate embodiments, the handle 50 may be coupled directly to the intermediate frame 16. The position sensor 52 may comprise a 3-D accelerometer, a 3-D gyroscope, an inclinometer, or other suitable type of sensor. Although only one handle 50 is shown in FIG. 1, it is contemplated that, in some embodiments, the handle assembly 34 may comprise a second movable handle 50 and a second position sensor 52 arranged to sense positioning of the second handle 50 (see FIG. 2).

As will be discussed in greater detail below, when a user pushes in a forward direction or in a reverse direction on one or both of handles 50, the drive system 48 drives one or more of the drive wheels 46 such that the patient transport apparatus 10 moves in the forward or reverse direction. It should be appreciated that the description set forth herein refers to forward and reverse movement, but other movement is also possible in some embodiments.

The patient transport apparatus 10 further comprises a lift system 58 (FIG. 2) having one or more lifts 56. The lifts 56 are adapted to raise and lower the intermediate frame 16 with respect to the base 14. The lifts 56 may comprise actuators A, such as hydraulic actuators, electro-hydraulic actuators, electric actuators, or other suitable types of actuators. The actuators A may be rotary actuators, linear actuators, or other suitable type. As will be discussed in greater detail below, the lifts 56 are controlled by one or more controllers.

Figure 2:
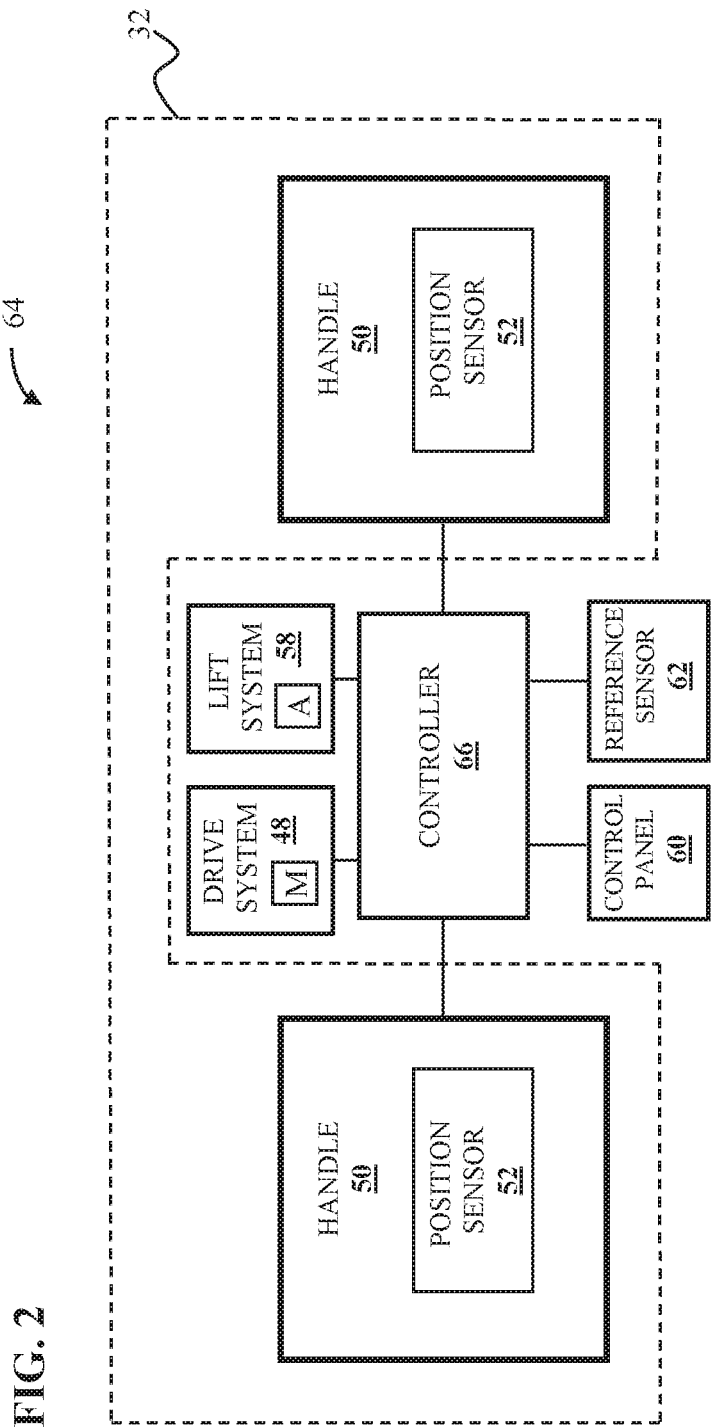
FIG. 2 is a block diagram of a control system usable with the patient transport apparatus of FIG. 1.

The patient transport apparatus 10 further comprises a control panel 60 (see FIGS. 1 and 2). The control panel 60 has a plurality of controls, such as buttons or other type of user input devices, that allow a user to control various of the powered and/or electronic functions of the patient transport apparatus 10, for example, to control the lift system 58 in order to change a height of the intermediate frame 16 with respect to the base 14. The control panel 60 may also comprise controls for controlling other functions.

The patient transport apparatus 10 further comprises a reference sensor 62 arranged to sense inclination of the support structure 12. The reference sensor 62 may comprise an accelerometer, a 3-D accelerometer, a 3-D gyroscope, an inclinometer, or other suitable sensor. In one embodiment, the reference sensor 62 may be integrated into the intermediate frame 16. In another embodiment, the reference sensor 62 may be integrated into or otherwise coupled to the base 14. Other suitable locations for the reference sensor 62 are also contemplated.

The patient transport apparatus 10 further comprises a control system 64 to control operation of the patient transport apparatus 10 and the functions described herein. The sensors 52, 62 are considered part of the control system 64. In one embodiment, the control system 64 is integrated into the handle assembly 34.

The control system 64 is illustrated in greater detail in FIG. 2. The control system 64 comprises a controller 66 that is in communication with the handle assembly 34 that is used to control the drive system 48. The controller 66 is also in communication with the lift system 58 of the patient transport apparatus 10. The drive system 48, as noted previously, comprises one or more motors M that are used to drive one or more of the drive wheels 46. The lift system 58, as also noted previously, comprises one or more actuators A for powering the lifts 56, which raise and lower the intermediate frame 16 with respect to the base 14.

In one embodiment, the controller 66 is a microcontroller. It will be understood, however, that the controller 66 may take on other forms. In general, the controller 66 may include one or more microprocessors, microcontrollers, field programmable gate arrays, systems on a chip, volatile or nonvolatile memory, discrete circuitry, and/or other hardware, software, or firmware that is capable of carrying out the functions described herein. Such components can be physically configured in any suitable manner, such as by mounting them to one or more circuit boards, or arranging them in other manners, whether combined into a single unit or distributed across multiple units. The instructions followed by the controller 66 in carrying out the functions described herein, as well as the data necessary for carrying out these functions, are stored in a memory (not labeled) accessible to the controller 66.

Figure 3:
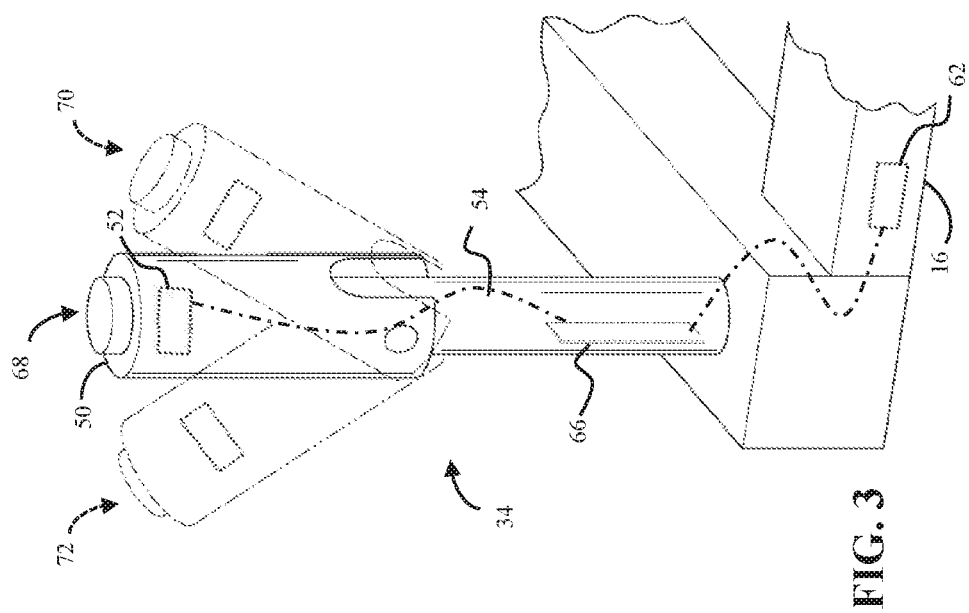
FIG. 3 is a perspective view of an illustrative embodiment of a handle assembly of the patient apparatus of FIG. 1.

As shown in FIG. 1, the handle assembly 34 is positioned at the head end of the patient transport apparatus 10 and comprises handles 50. Referring now to FIG. 3, the handle 50 is movable from a home position 68 to one or more forward operational positions 70. The handle 50 is further movable from the home position 68 to one or more rearward operational positions 72. A biasing device (not shown) may bias the handle 50 toward the home position 68 from any of the forward or rearward operational positions.

Each handle 50 comprises a position sensor 52. The position sensor 52 is coupled to the controller 66, as is the reference sensor 62. Contoller 66 is adapted to control the drive system 48 in response to signals received from the reference sensor 62 and the position sensor 52. The reference sensor 62 is arranged to sense a reference angle α (See FIGS. 3A-3C). The reference angle α, in the embodiment shown, is the angle of the intermediate frame 16 with respect to gravity G.

Figure 3A:
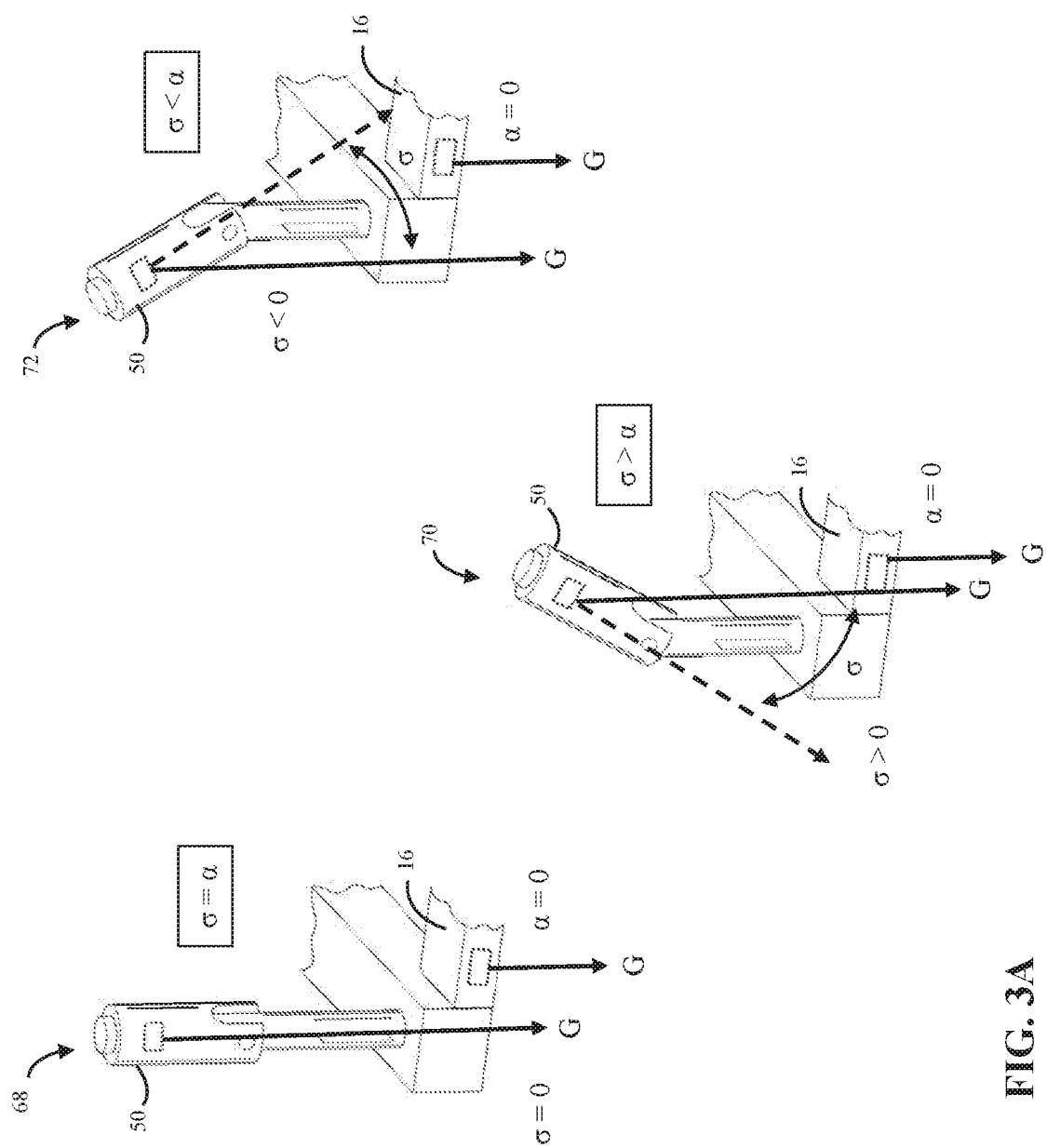
FIGS. 3A-3C illustrate perspective view of various inclinations of an intermediate frame of the patient transport apparatus of FIG. 1.

In FIG. 3A the reference angle α is zero, since the intermediate frame 16 is oriented horizontally. However, should the intermediate frame 16 (and/or the base 14 or other component to which the reference sensor 62 is attached) deviate from horizontal, such as when the patient transport apparatus 10 is on an incline (FIG. 3B) or decline (FIG. 3C), then a non-zero reference angle α would be detected. In this case, the handle 50 would no longer be in a vertical orientation with respect to gravity G when in the home position 68.

The reference sensor 62 sends a reference signal indicating the reference angle α to the controller 66. The position sensor 52 is arranged to sense a position angle σ. The position angle σ, in the embodiment shown, is the angle of the handle 50 with respect to gravity G. The position sensor 52 sends a position signal indicating the position angle σ to the controller 66. Examples of varying position angles σ are shown in FIGS. 3A-3C based on the position of the handle 50.

In other embodiments, the position sensor 52 and the reference sensor 62 could be located with respect to the handle 50 and the support structure 12 in other ways to provide suitable signals for use in controlling the drive system 48. For example, if the patient transport apparatus 10 can be placed in Trendelenburg and/or reverse Trendelenburg positions, a second reference sensor 62 (e.g., an accelerometer) could be located on the base 14 to sense any inclination of the floor surface 36 and the reference sensor 62 on the intermediate frame 16 could be used to sense the Trendelenburg and/or reverse Trendelenburg positions (e.g., Trend angles). The reference sensors 62 on the base 14 and the intermediate frame 16 could be arranged to normally have similar readings, i.e., when the intermediate frame 16 and the base 14 are parallel (no Trend), but could indicate Trendelenburg positioning when their readings are different. The reference sensors 62 would transmit associated signals to the controller 66 so that the controller 66 can compensate for such Trendelenburg positioning.

The controller 66 determines, based on the reference and position signals received from the reference sensor 62 and the position sensor 52, respectively, if the handle 50 is: (1) at the home position 68, (2) has moved from the home position 68 to one of the forward operational positions 70, or (3) has moved from the home position 68 to one of the rearward operational positions 72.

Figure 3B:
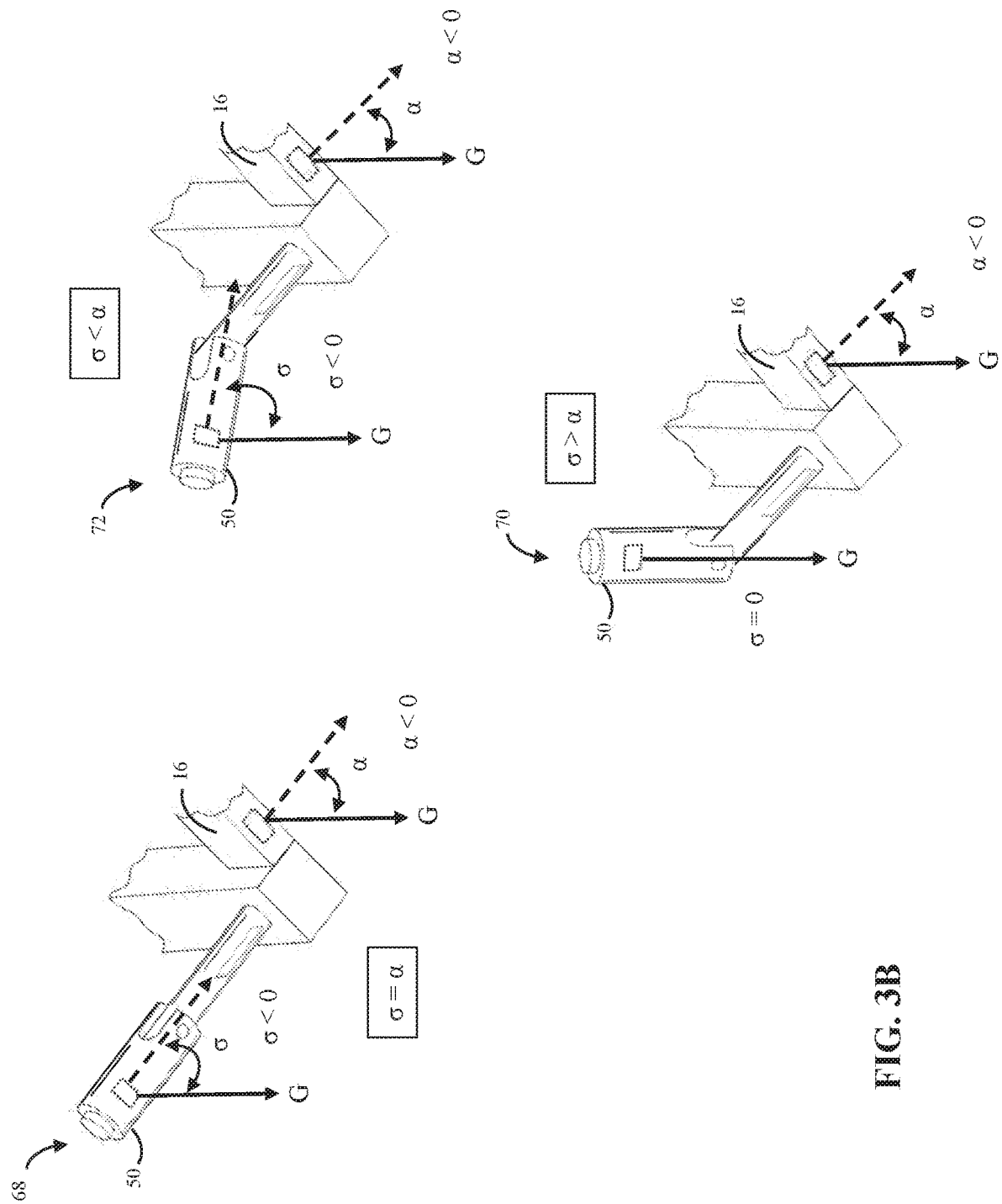
Figure 3C:
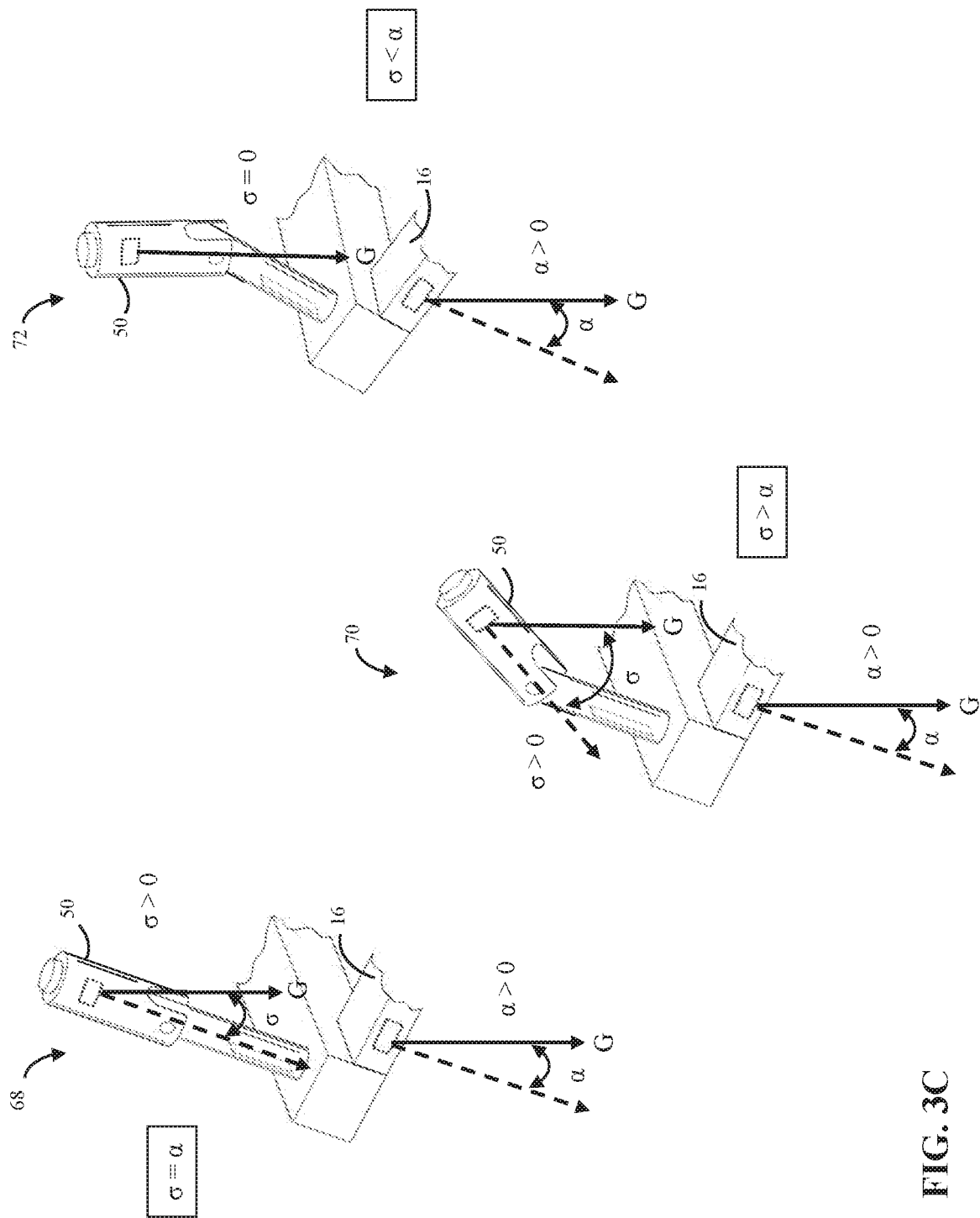

Referring to FIGS. 3A-3C, various inclinations of the intermediate frame 16 are shown for illustration. In each case, the controller 66 is configured to determine if the handle 50 is at the home position 68 based on the position signal and the reference signal regardless of whether the intermediate frame 14 is horizontally oriented or is on an incline or on a decline.

In the embodiment shown in FIG. 3 and FIGS. 3A-3C, based on the geometry of the handle 50 and the intermediate frame 16, and the locations of the position sensor 52 and the reference sensor 62, the controller 66 is configured to determine that the handle 50 is at: (a) the home position 68 when the position signal and the reference signal indicate that the position angle σ is equal to the reference angle α; (b) a forward operational position 70 when position signal and the reference signal indicate that the position angle σ is greater than the reference angle α; or (3) a rearward operational position 72 when position signal and the reference signal indicate that the position angle σ is less than the reference angle α. However, in other embodiments where the locations of the position sensor 52 and the reference sensor 62 are not oriented the same way to read zero when horizontal, these positions may be indicated by different angle correlations, for instance, the forward operational position 70 may be indicated when the position angle σ is less than the reference angle α and the rearward position 72 may be indicated when the position angle σ is greater than the reference angle α.

The following formulas illustrate one method of determining the position of the handle 50 in FIG. 3A (angle values are for illustration purposes only):

Home Position: $\sin(\alpha-\sigma)=\sin(0°-0°)=\sin(0°)=0$

Forward Position: $\sin(\alpha-\sigma)=\sin(0°-15°)=\sin(-15°)=-0.2588$

Rearward Position: $\sin(\alpha-\sigma)=\sin(0°-(-15°))=\sin(15°)=+0.2588$

The following formulas illustrate the same method of determining the position of the handle 50 when the intermediate frame 16 is inclined in FIG. 3B (angle values are for illustration purposes only):

Home Position: $\sin(\alpha-\sigma)=\sin(-15°-(-15°))=\sin(0°)=0$

Forward Position: $\sin(\alpha-\sigma)=\sin(-15°-0°)=\sin(-15°)=-0.2588$

Rearward Position: $\sin(\alpha-\sigma)=\sin(-15°-(-30°))=\sin(15°)=+0.2588$

The following formulas illustrate the same method of determining the position of the handle 50 when the intermediate frame 16 is declined in FIG. 3C (angle values are for illustration purposes only):

Home Position: $\sin(\alpha-\sigma)=\sin(15°-15°)=\sin(0°)=0$

Forward Position: $\sin(\alpha-\sigma)=\sin(15°-30°)=\sin(-15°)=-0.2588$

Rearward Position: $\sin(\alpha-\sigma)=\sin(15°-0°)=\sin(15°)=+0.2588$

When handle 50 is determined to be in home position 68, controller 66 is operable to immobilize drive system 48, for example, by stopping drive wheel 46 from further motion if drive wheel 46 is already in motion. When the handle 50 is determined to be in one of the forward operational positions 70, the controller 66 is operable to direct the drive system 48 to propel the patient transport apparatus 10 in a forward direction. When the handle 50 is determined to be in one of the rearward operational positions 72, the controller 66 is operable to direct the drive system 48 to propel the patient transport apparatus 10 in a rearward direction.

The controller 66 is further configured to direct the drive system 48 to propel the patient transport apparatus 10 at an operational speed. The operational speed is based on a differential between the position angle σ and the reference angle α. The operational speed increases when the differential between the position angle σ and the reference angle α increases. Conversely, the operational speed decreases when the differential between the position angle σ and the reference angle α decreases.

Figure 4:
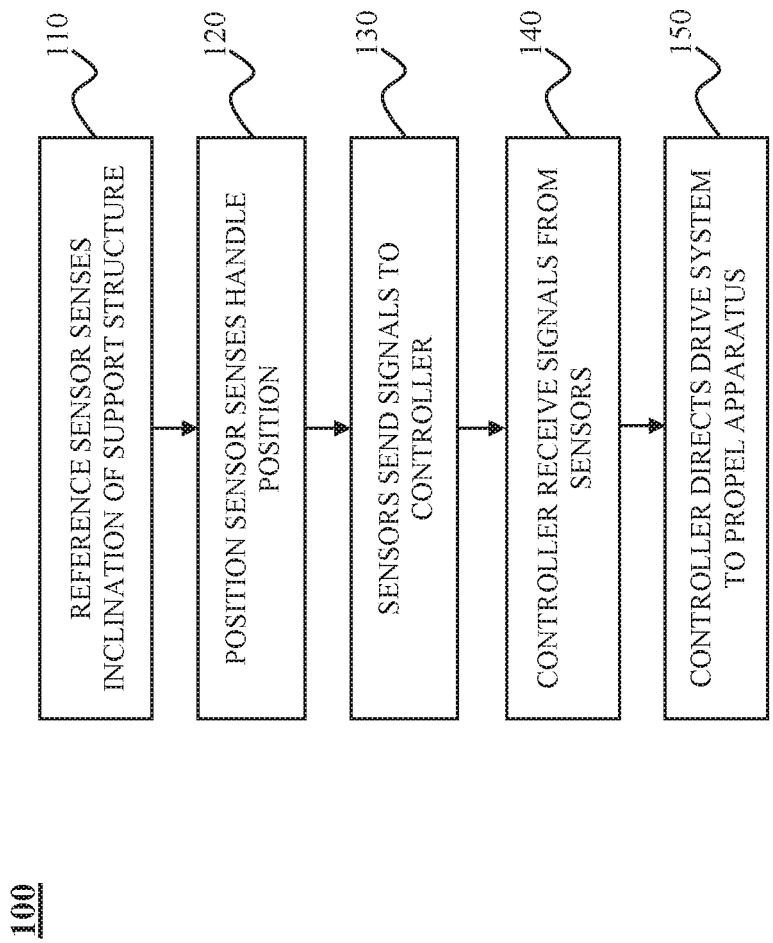
FIG. 4 is a flow diagram of a method for controlling a drive system to propel the patient transport apparatus of FIG. 1 along a floor surface.

Referring now to FIG. 4, a method 100 for controlling a drive system to propel a patient transport apparatus along a floor surface is shown. At a first step 110, the reference sensor 62 senses reference angle α comprising an inclination of the support structure 12. The reference angle α comprises an angle of the base 14 with respect to gravity. At a second step 120, the position sensor 52 senses a position angle σ comprising a position of the handle 50. The position angle σ comprises an angle of the handle 50 with respect to gravity. At a third step 130, the reference sensor 62 and the position sensor 52 send signals indicating the reference angle α and the position angle σ to the controller 66. At a fourth step 140, the controller 66 receives the signals. At a fifth step 150, the controller 66 directs the drive system 48 to propel the patient transport apparatus 10 along the floor surface 36 based on the signals.

In an embodiment with two handles 50, it is contemplated that the user may be required to apply pressure to both handles 50 in the same direction (forward, rearward, to home) in order to cause the controller 66 to direct the drive system 48 to propel the patient transport apparatus 10.

In an alternate embodiment with two handles 50, it is contemplated that the drive wheel assembly 44 may be comprised of two independently controlled drive wheels or drive tracks, one controlled by each handle 50. In this embodiment, applying a different position to each handle 50 may result in varying movements of the patient transport apparatus 10. For instance, pushing one handle 50 while pulling the other handle 50 may cause the patient transport apparatus 10 to turn in one direction, and vice versa for the other direction. It will be appreciated that other configurations may be possible.

It is to be appreciated that the terms "include," "includes," and "including" have the same meaning as the terms "comprise," "comprises," and "comprising."

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention is intended to be defined in the independent claims, with specific features laid out in the dependent claims, wherein the subject-matter of a claim dependent from one independent claim can also be implemented in connection with another independent claim.

What is claimed is:

1. A patient transport apparatus for transporting a patient over a surface, the patient transport apparatus comprising:
   a support structure comprising a base, a patient support surface, and a reference sensor arranged to sense inclination of the support structure;
   a drive system coupled to the support structure and operable to propel the patient transport apparatus;
   a handle assembly operable by a user to control operation of the drive system, the handle assembly comprising a handle movable relative to the base and a position sensor arranged to sense positioning of the handle; and
   a controller coupled to the reference sensor and the position sensor, and adapted to control the drive system in response to signals received from the reference sensor and the position sensor.

2. The patient transport apparatus of claim 1, wherein:
   the reference sensor is arranged to sense a first angle of the base with respect to gravity and send a first signal indicating the first angle to the controller; and
   the position sensor is arranged to sense a second angle of the handle with respect to gravity and send a second signal indicating the second angle to the controller.

3. The patient transport apparatus of claim 2, wherein the handle is movable from a home position to forward operational positions and the controller is configured to:
   determine, based on the first and second signals, if the handle has moved from the home position to one of the forward operational positions,
   immobilize the drive system in response to the handle being at the home position, and
   direct the drive system to propel the patient transport apparatus in a forward direction in response to the handle being at one of the forward operational positions.

4. The patient transport apparatus of claim 3, wherein the handle is movable from the home position to rearward operational positions and the controller is configured to:
   determine, based on the first and second signals, if the handle has moved from the home position to one of the rearward operational positions, and
   direct the drive system to propel the patient transport apparatus in a rearward direction in response to the handle being at one of the rearward operational positions.

5. The patient transport apparatus of claim 2, wherein the controller is configured to direct the drive system to propel the patient transport apparatus at an operational speed, wherein the operational speed is based on a differential between the first angle and the second angle.

6. The patient transport apparatus of claim 5, wherein the operational speed increases when the differential between the first angle and the second angle increases.

7. The patient transport apparatus of claim 5, wherein the operational speed decreases when the differential between the first angle and the second angle decreases.

8. The patient transport apparatus of claim 3, wherein the controller is configured to determine that the handle is at the home position when the first signal and the second signal indicate that the first angle is equal to the second angle.

9. The patient transport apparatus of claim 8, wherein the controller is configured to determine if the handle is at the home position based on the first signal and the second signal when the base is on an incline or decline.

10. The patient transport apparatus of claim 1, wherein the reference sensor comprises an accelerometer.

11. The patient transport apparatus of claim 1, wherein the position sensor comprises an accelerometer.

12. The patient transport apparatus of claim 1, further comprising support wheels coupled to the base and swivelable about swivel axes.

13. The patient transport apparatus of claim 1, wherein the drive system comprises a drive wheel.

14. The patient transport apparatus of claim 1, wherein the drive system is operable to propel the patient transport apparatus in one or more of a forward and rearward direction.

15. The patient transport apparatus of claim 1, wherein the support structure further comprises a post fixed to the base and coupled to the handle.

16. The patient transport apparatus of claim 1, wherein the handle assembly comprises a second handle movable relative to the base and a second position sensor arranged to sense positioning of the second handle, the controller coupled to the second position sensor and adapted to control the drive system in response to signals received from the reference sensor and the position sensors.

17. A method for controlling a drive system to propel a patient transport apparatus along a floor surface, the patient transport apparatus having a support structure with a base, a patient support surface, and a handle operable by a user to operate the drive system, the method comprising the steps of:
- sensing inclination of the support structure;
- sensing positioning of the handle; and
- controlling the drive system in response to the sensed inclination of the support structure and the sensed positioning of the handle to propel the patient transport apparatus along the floor surface.

18. The method of claim 17, wherein;
- sensing the inclination of the support structure comprises sensing a first angle of the base with respect to gravity and sending a first signal indicating the first angle to a controller; and
- sensing the positioning of the handle comprises sensing a second angle of the handle with respect to gravity and sending a second signal indicating the second angle to the controller.

* * * * *